(12) United States Patent
Farkas et al.

(10) Patent No.: US 6,530,882 B1
(45) Date of Patent: Mar. 11, 2003

(54) ENDOSCOPE HAVING MICROSCOPIC AND MACROSCOPIC MAGNIFICATION

(75) Inventors: Richard Farkas, Bloomfield Hills, MI (US); Richard Fisher, Ann Arbor, MI (US); Steven Henke, Canton, MI (US)

(73) Assignee: Inner Vision Imaging, L.L.C., Farmington Hills, MI (US)

(*) Notice: Subject to any disclaimer, the term of this patent is extended or adjusted under 35 U.S.C. 154(b) by 215 days.

(21) Appl. No.: 09/608,321

(22) Filed: Jun. 30, 2000

(51) Int. Cl.[7] .............................. A61B 1/002; A61B 1/06
(52) U.S. Cl. ........................................ 600/168; 600/178
(58) Field of Search .................................. 600/108, 109, 600/168, 178, 121, 138, 473, 475

(56) References Cited

U.S. PATENT DOCUMENTS

| | | | |
|---|---|---|---|
| 4,269,485 A | 5/1981 | Yamashita et al. | 350/469 |
| 4,300,812 A | 11/1981 | Nakahashi | 350/42 |
| 4,312,572 A | 1/1982 | Yamashita et al. | 350/423 |
| 4,385,810 A | 5/1983 | Hamou | 350/520 |
| 4,639,772 A | 1/1987 | Sluyter et al. | 358/98 |
| 4,664,486 A | 5/1987 | Landre et al. | 350/414 |
| 4,666,262 A | 5/1987 | Zobel | 350/518 |
| 4,704,007 A | 11/1987 | Landre et al. | 350/414 |
| 4,821,117 A | 4/1989 | Sekiguchi | 358/98 |
| 4,905,082 A | 2/1990 | Nishigaki et al. | 358/98 |
| 5,045,936 A * | 9/1991 | Lobb | 348/135 |
| 5,200,819 A * | 4/1993 | Nudelman et al. | 348/46 |
| 5,255,087 A | 10/1993 | Nakamura et al. | 358/98 |
| 5,396,366 A | 3/1995 | Brown et al. | 359/435 |
| 5,418,645 A | 5/1995 | Coath et al. | 359/676 |
| 5,532,873 A | 7/1996 | Dixon | 359/388 |
| 5,582,573 A | 12/1996 | Hori et al. | 600/167 |
| 5,605,531 A * | 2/1997 | Lane et al. | 348/74 |
| 5,659,642 A | 8/1997 | King et al. | 385/16 |
| 5,719,700 A | 2/1998 | Corcuff et al. | 359/368 |
| 5,737,121 A | 4/1998 | Dixon | 359/388 |
| 5,742,419 A | 4/1998 | Dickensheets et al. | 359/201 |
| 5,788,639 A | 8/1998 | Zavislan et al. | 600/476 |
| 5,836,869 A | 11/1998 | Kudo et al. | 600/173 |
| 5,836,877 A | 11/1998 | Zavislan | 600/407 |
| 5,863,287 A | 1/1999 | Segawa | 600/121 |
| 5,910,816 A | 6/1999 | Fontenot et al. | 348/65 |
| 5,995,867 A | 11/1999 | Zavislan et al. | 600/476 |
| 5,997,472 A | 12/1999 | Bonnell et al. | 600/109 |
| 6,007,482 A | 12/1999 | Madni et al. | 600/115 |
| 6,013,025 A | 1/2000 | Bonne et al. | 600/160 |
| 6,028,622 A | 2/2000 | Suzuki | 348/65 |
| 6,038,067 A * | 3/2000 | George | 359/368 |
| 6,059,721 A | 5/2000 | Rudischhauser et al. | 600/167 |
| 6,155,973 A * | 12/2000 | Howes et al. | 359/683 |
| 6,450,949 B1 * | 9/2002 | Farkas et al. | 600/168 |

* cited by examiner

Primary Examiner—John P. Leubecker
(74) Attorney, Agent, or Firm—Gifford, Krass, Groh, Sprinkle, Anderson & Citkowski, P.C.

(57) ABSTRACT

An endoscope assembly is disclosed having a housing adapted to be manipulated by medical personnel, such as a surgeon. An elongated lens tube has one end secured to the housing while an elongated stage is removably secured to the housing so that the stage encompasses and is coaxial with the tube. The stage together with the lens tube are adapted for insertion into the cavity of a body. A lens assembly provided within the lens tube relays the optical image from the free end of the stage to the housing. A lens assembly within the housing, furthermore, varies the magnification of the image between macroscopic magnification and microscopic magnification in which tissue may be examined on a cellular level. For macroscopic magnification, white light is transmitted through the lens tube as well as reflected back from the target tissue through the lens tube and to the housing. For microscopic examination, laser radiation is utilized in lieu of the white light illumination. A line scanning confocal assembly contained within the housing enables microscopic examination of the target tissue at varying levels into the tissue from the end of the stage.

21 Claims, 9 Drawing Sheets

ENDOSCOPE HAVING MICROSCOPIC AND MACROSCOPIC MAGNIFICATION

BACKGROUND OF THE INVENTION

I. Field of the Invention

The present invention relates generally to medical instruments and, more particularly, to an endoscope.

II. Discussion of Related Art

Laparoscopic surgery has enjoyed increasing acceptance, particularly for surgery involving the abdominal cavity. In such surgery, one or more incisions are made through the patient's skin. Thereafter, various medical instruments, including endoscopes, are inserted through the incisions and into a body cavity, such as the abdominal cavity.

In order for the surgeon to see into the abdominal cavity, the surgeon typically uses an endoscope which is inserted through a cannula and into the abdominal cavity. The previously known endoscopes typically comprise an elongated tube having one or more fixed lenses. These lenses provide an optical view of the interior of the body cavity to an eyepiece or other display means accessible to the surgeon outside the body. Illumination for the endoscope is typically provided by optical fibers which extend along the length of the endoscope and form a ring around the outer periphery of the free end of the endoscope. The opposite ends of the optical fibers are connected to a light source.

These previously known endoscopes, however, have all suffered from a number of disadvantages. Perhaps the most significant disadvantage of these previously known endoscopes is that, since the optical lenses are fixed within the endoscope, the field of magnification for the endoscope remains constant. Typically, these previously known endoscopes utilize lenses which provide low or macroscopic magnification (hereafter collectively referred to as macroscopic magnification) within the body cavity so that a relatively wide field of view of the body cavity is obtained.

In many situations, however, it would be desirable for the endoscope to provide microscopic magnification of organs contained within the body cavity. For example, in certain situations where cancerous growths within body organs are suspected, the macroscopic magnification provided by the previously known endoscopes is insufficient to examine the organ tissue in sufficient detail to determine whether the tissue abnormality is cancerous or benign. As a result, it has been necessary for the surgeon to remove the tissue to perform a biopsy and, in many cases, to remove the entire organ for subsequent pathological examination outside the body.

The removal of biological tissue from the body and subsequent pathological examination outside the body suffers from two important disadvantages. First, in the event that the organ abnormality is benign, the biopsy and possible removal of the entire organ from the body results in unnecessary harm and even loss of organ function to the patient. Second, since the subsequent pathological examination of the body tissue oftentimes occurs long after the end of the operation, in the event that the pathological examination reveals a cancerous growth within the body tissue, it is oftentimes necessary for the surgeon to re-enter the body cavity and remove additional body tissue in an attempt to completely eradicate the cancer. This disadvantageously, however, subjects the patient to a second operation.

An additional disadvantage of previously known endoscopes is that the illumination and viewing paths are separate and each path uses only a portion of the available diameter of the endoscope. It would be desirable to use the entire available diameter of the endoscope for the viewing path as it would permit the use of optical lenses with larger apertures, thus providing increased resolution in the optical image formed by the lenses without requiring an increase in the overall diameter of the endoscope.

SUMMARY OF THE PRESENT INVENTION

The present invention provides an endoscope for use in laparoscopic surgery which overcomes all of the above-mentioned disadvantages of the previously known devices.

The endoscope of the present invention has a lens assembly forming an optical path within an endoscope tube, in which the optical path is shared by both the light used to illuminate an object, such as tissue within a body cavity, and the light collected from the object. The endoscope tube is joined to an external housing that has an additional optical assembly; the combined endoscope tube and housing optics form images on one or more detectors within the housing that convert the images into electronic signals. Cables are provided for an electronic and optical interface between the housing and an external control system such as a personal computer, power supplies, and illumination sources.

The magnification achieved by the endoscope assembly can be varied between macroscopic, or low, magnification and microscopic, or high, magnification. Macroscopic magnification is utilized to provide an optical view to the surgeon of a relatively wide area within the body cavity whereas in the microscopic magnification mode, the system is capable of resolving structure at the cellular level. In microscopic mode, the system provides high resolution imaging not only of the surface layer of body tissue, but also of layers beneath the surface by means of a confocal assembly contained within the housing. In-depth imaging is enhanced by the use of near-infrared illumination, at which wavelengths body tissue is typically more transparent than at visible wavelengths.

The optical assembly in the housing includes separated or partially separated paths for the macroscopic and microscopic imaging modes. Beamsplitters are provided to split the combined optical path of the endoscope lens into the separated paths of the housing optics, and optionally to recombine the paths onto a single CCD camera. The macroscopic magnification path uses white light illumination and preferably a three-chip CCD detector to provide full color imaging. The light source used in the microscopic magnification mode is preferably a laser diode operating in the near infrared region of the spectrum at a wavelength of about 950 nm. The microscopic magnification path in the housing includes a confocal assembly to provide high definition imagery both at the surface of the tissue and of thin sections deep within the tissue. The confocal assembly includes scanning means, which preferably operate in a line-scanning format, although other scanning techniques may be used such as point scanning or Nipkow disk scanning.

In macroscopic mode, magnification changes occur by moving lenses in the housing, the endoscope tube, or both as the endoscope is moved closer to the object of interest. Changes in magnification also take place on switching between white light and laser light illumination. Filters, polarizers, and retarders are provided as appropriate to control the spectral and polarization characteristics of the illumination and imaging light.

The endoscope assembly includes an additional tube, or stage, that slides over the endoscope tube and removably attaches to the housing. The combined stage and endoscope tube are adapted for insertion into a body cavity through a cannula. The endoscope tube is movable with respect to the stage between an extended and a retracted position by drive means contained within the housing.

The stage has a window that provides an optical interface between the body cavity and the endoscope optics. The window can be placed directly against body tissue, and the endoscope tube can be moved in a direction perpendicular to the window to focus at different depths within the tissue. When the endoscope tube is in the retracted position in microscopic mode, the endoscope optics are focused at the outer surface of the stage window, which is in contact with the tissue surface; when the endoscope tube is extended, the focus moves away from the window to a depth below the surface of the tissue. A chamber filled with a liquid, preferably a saline solution, having a predetermined refractive index is provided between the stage window and the endoscope optics to approximately match the refractive index of body tissue. A reservoir is provided to allow the liquid-filled chamber to expand and contract as the endoscope tube is retracted or extended.

The stage also provides a sterile barrier between the body cavity and the endoscope tube. Because of its simplicity, the stage may be readily sterilized between uses or it may be disposable.

In the preferred embodiment of the invention, the optical images formed by the optical assemblies of the endoscope apparatus are focused onto CCD detectors and transmitted as electronic signals to a computer system. The computer system, in turn, communicates the digitized images via a network and/or telephone lines to a pathologist who may be remote from the patient. Consequently, the pathologist is capable of viewing the images through the endoscope on a real-time basis. Since the endoscopic imaging system of the present invention enables real-time pathological examination and diagnosis of suspect tissue, unnecessary biopsies and/or organ removal are prevented.

BRIEF DESCRIPTION OF THE DRAWING

A better understanding of the present invention will be had upon reference to the following detailed description, when read in conjunction with the accompanying drawing, wherein like reference characters refer to like parts throughout the several views, and in which.

DETAILED DESCRIPTION OF A PREFERRED EMBODIMENT OF THE PRESENT INVENTION

Figure 1:
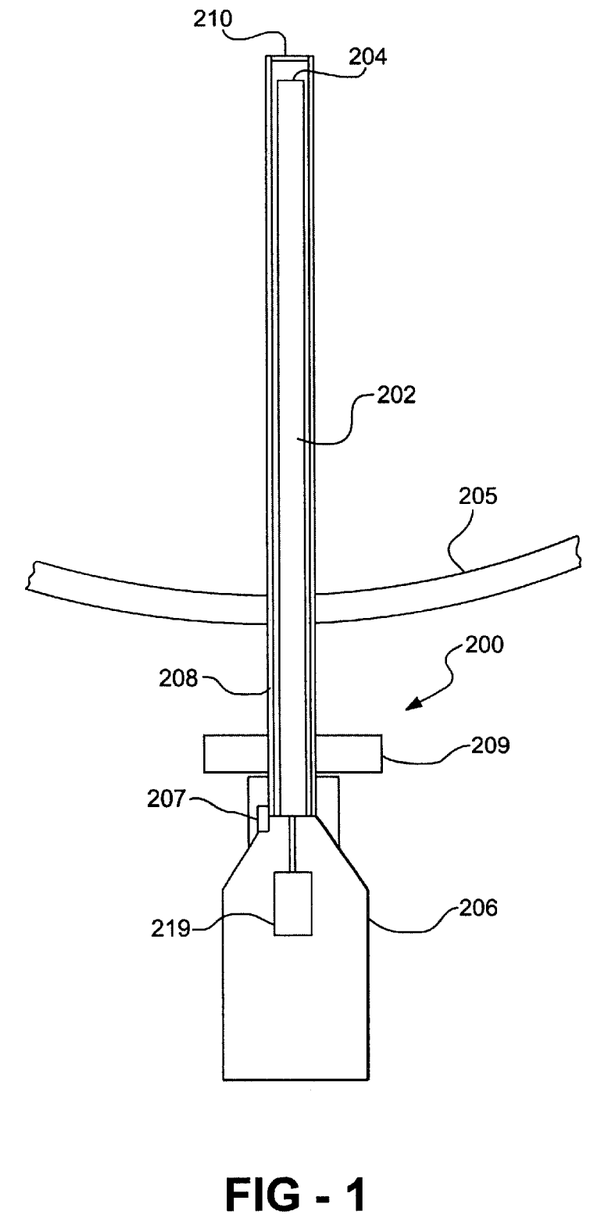
FIG. 1 is a diagrammatic view illustrating a preferred embodiment of the present invention.

With reference first to FIG. 1, a preferred embodiment of the endoscope assembly 200 of the present invention is there shown. The endoscope 200 includes an elongated endoscope lens tube 202 having a free end 204 and an opposite end that is attached to a housing 206. The housing is designed to be manipulated by hand by the surgeon or other medical personnel, although it may alternatively be attached to a mechanical support or to a robotic arm. An elongated tubular stage 208 is dimensioned to be slidably received over the free end 204 of the lens tube 202 and is detachably secured to the housing 206 by a mechanical coupling 207, such as a bayonet coupling. The stage 208 has a transparent window 210 that is positioned over the free end 204 of the lens tube 202. The lens tube 202 together with the stage 208 is insertable into the patient 205 through a cannula while the housing 206 remains exterior of the patient.

Figure 2:
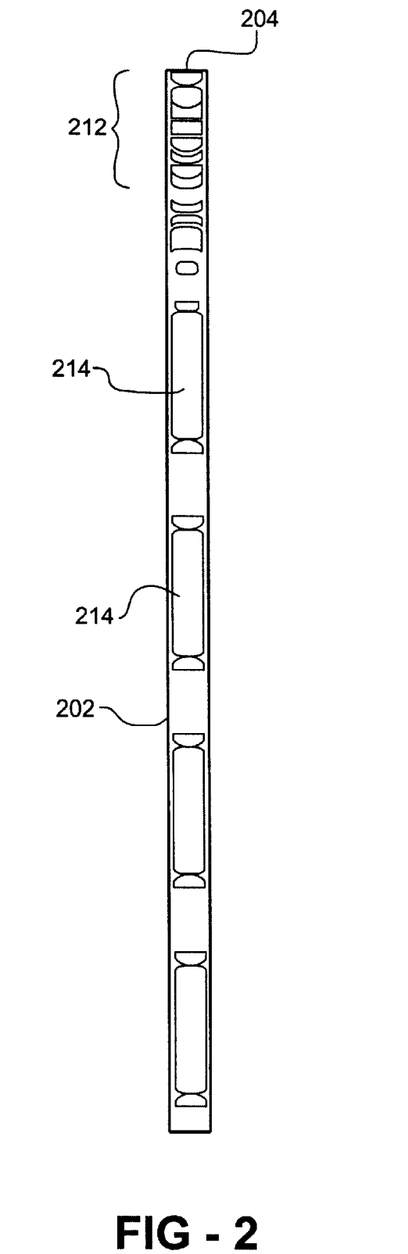
FIG. 2 is a diagrammatic view illustrating the lens tube and its contained lens assemblies for the preferred embodiment of the invention.
Figure 3:
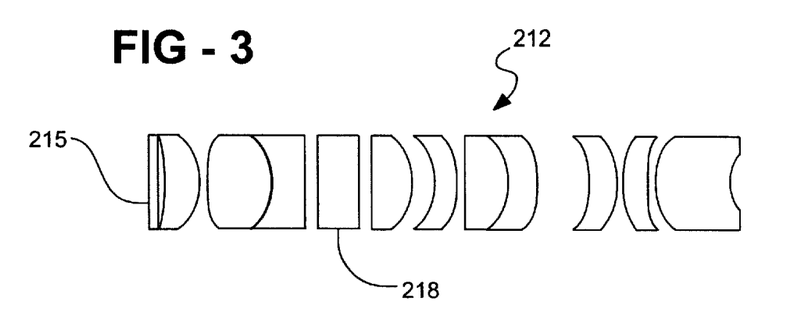
FIG. 3 is a diagrammatic view illustrating the lens assembly for the objective lens of the preferred embodiment of the invention.
Figure 4:
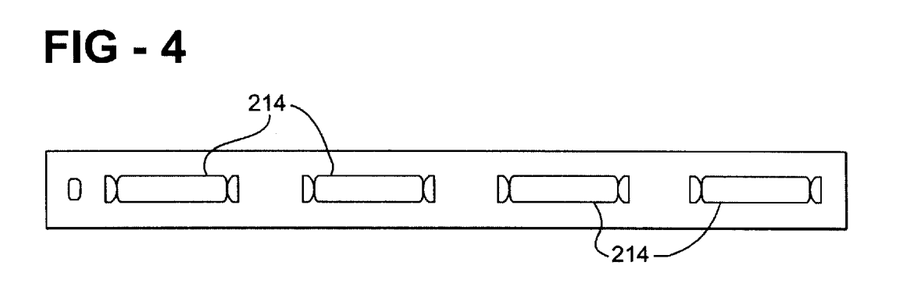
FIG. 4 is a diagrammatic view of the relay lens assembly for the preferred embodiment of the invention.

With reference now to FIGS. 2–4, a plurality of optical lenses are disposed within the lens tube 202 so that these lenses extend along the length of the lens tube 202. These lenses include an objective lens 212, best shown in FIG. 3, which extends inwardly into the lens tube 202 from the free end 204 of the lens tube 202. A window 215 is attached to the free end 204 of the lens tube to provide an optical interface into the space beyond the objective lens. One or more conventional relay lenses 214 are contained within the lens tube 202 at spaced intervals from the objective lens 212 to the housing 206. The objective lens 212, together with the relay lens or lenses 214, provides an optical image of the optical view at the free end 204 of the lens tube 202 to the housing 206.

Figure 5A:
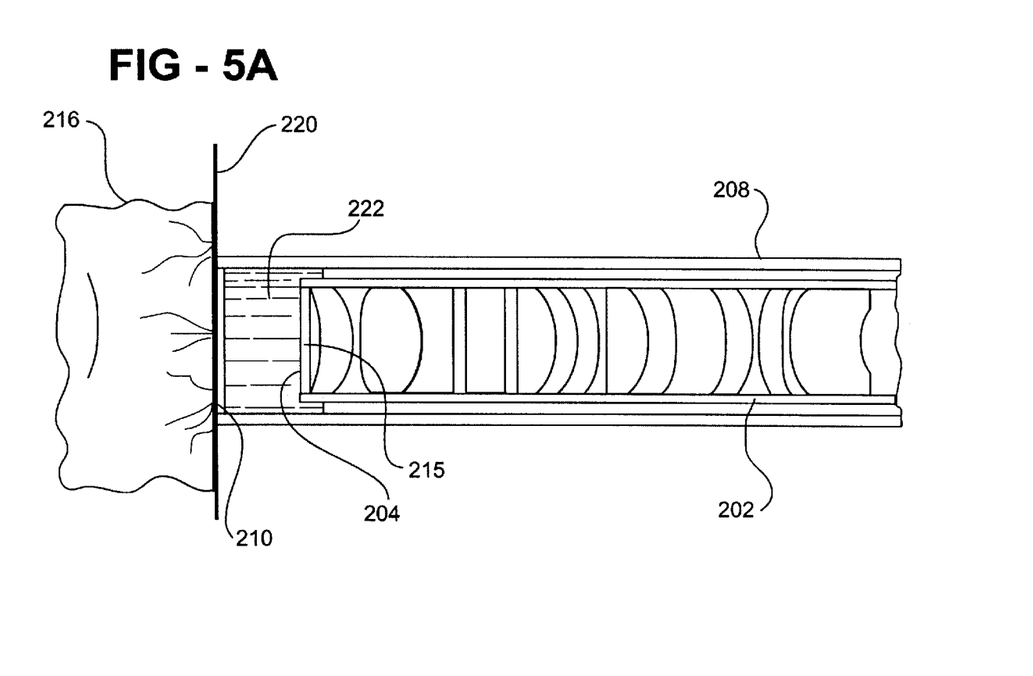
FIGS. 5A and 5B are diagrammatic views illustrating the free end of the lens tube for the preferred embodiment of the invention.
Figure 5B:
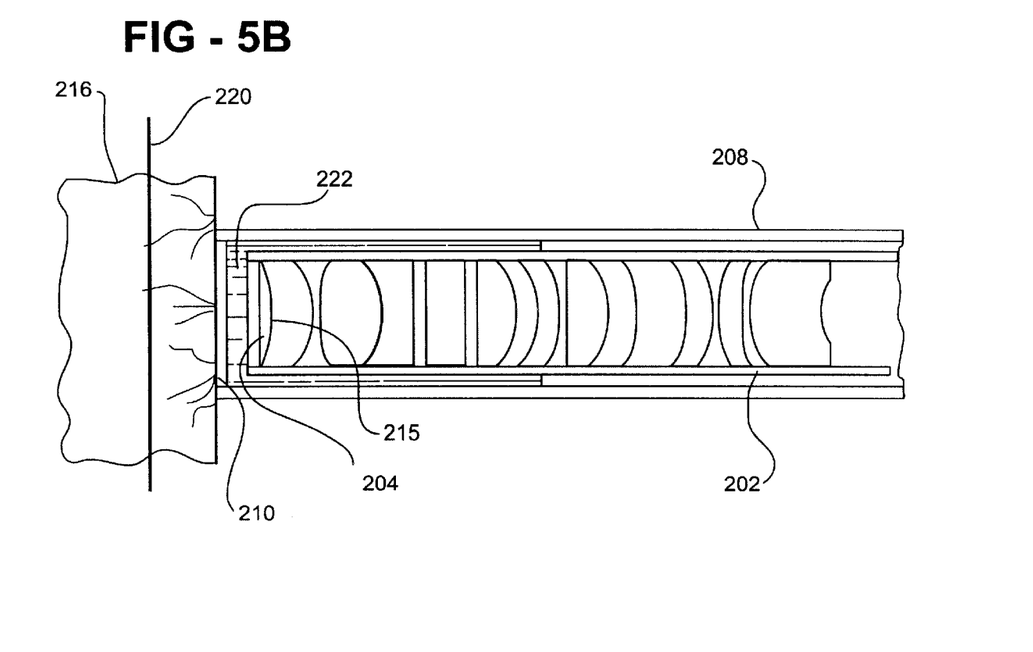

With reference now to FIGS. 5A and 5B, a diagrammatic view of the free end of the endoscope 200 is there shown in which the window 210 on the stage 208 is positioned against tissue 216 under inspection. The lens tube 202 is axially movable relative to the stage 208 from a retracted position shown in FIG. 5A to an extended position shown in 5B. As the lens tube is moved from the retracted position to the extended position, the object plane 220 shifts from the surface of the tissue 216 to a known depth within the tissue. Any conventional means 219 (FIG. 1), such as a stepper motor or manual knob, can be used to move the lens tube relative to the stage.

The stage 208 has a cylindrical collar 209 attached near the housing 206. The collar 209 forms a mounting structure through which the stage may be attached to a mechanical support such as a robotic arm.

A chamber 222 between the window 215 at the free end 204 of the lens tube 202 and the window 210 on the stage 208 is filled with a liquid, preferably a saline solution, having a refractive index that is approximately the same as the refractive index of the tissue being examined. When the lens tube is retracted or extended, the liquid is respectively drawn from or returned to a reservoir, maintaining a constant optical depth to the object being viewed and minimizing optical aberrations. The reservoir may be a separate bladder or simply the space between the lens tube 202 and the stage 208 as illustrated in FIG. 5B.

Figure 6:
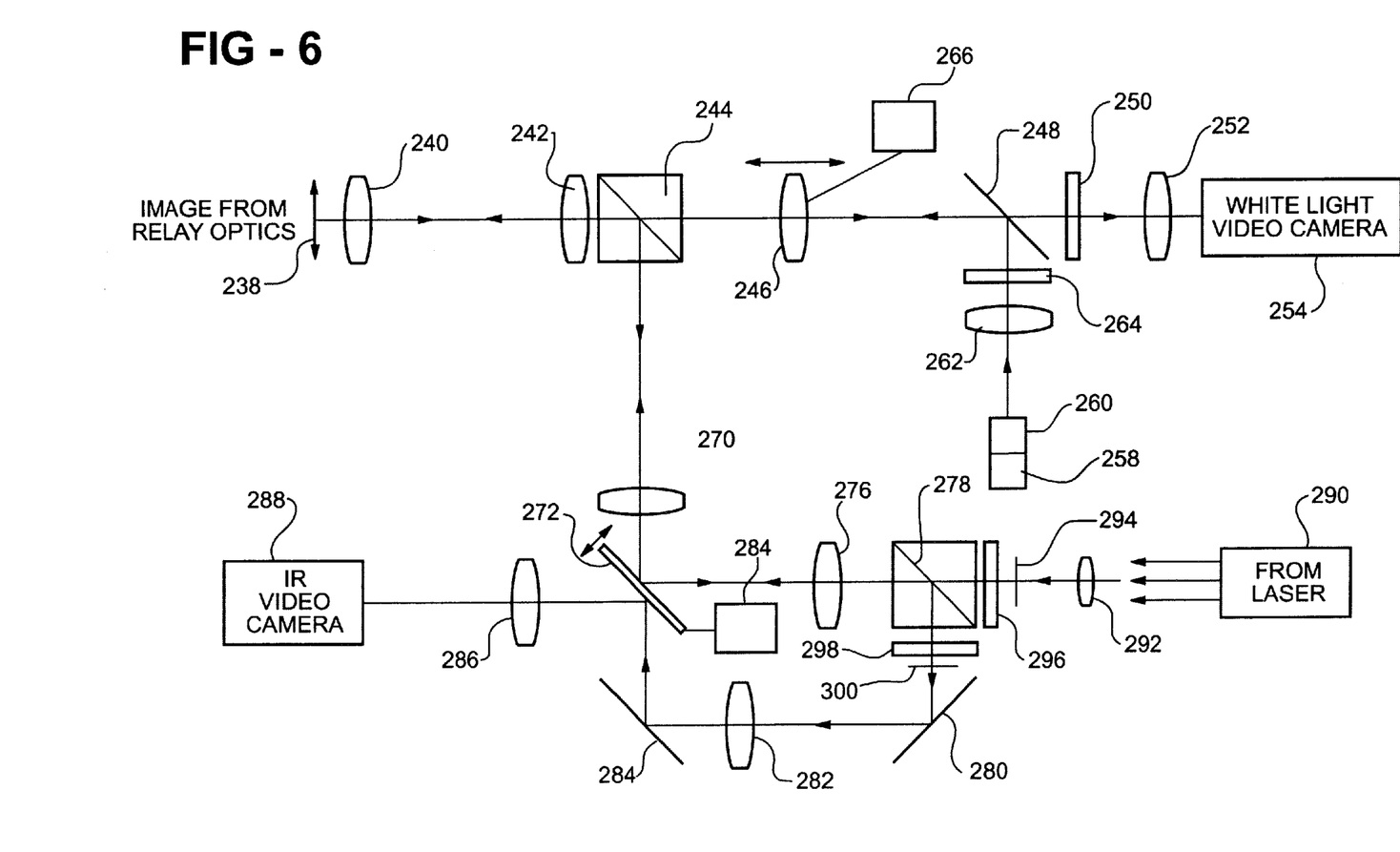
FIG. 6 is an optical diagrammatic view illustrating the preferred embodiment of the housing of the present invention.

FIG. 6 is an optical diagrammatic view of the housing lens assembly. This is best understood if the light path for the macroscopic and microscopic modes are described separately, beginning with the illumination source for each path.

Macroscopic Light Path

The illumination for the macroscopic light path is preferably from an arc lamp located remotely from the endoscope. This light source is suitably filtered, either at the lamp or in the housing, to remove infrared radiation. A fiber optic cable 258 transfers the light from the lamp to the housing. Lens 262 forms an image of the fiber optic face 260 at the pupil plane of the macroscopic path of the housing lens assembly. The illuminating light passes through lens 262 and plane polarizer 264, is reflected by beamsplitter 248, and is focused by lens 246. The illumination further passes through beamsplitter 244, collimating lens 242, and field lens 240, after which it passes through the lens tube 202 to illuminate the object being viewed.

Light returned from the object being viewed passes back through the lens tube 202 to the housing lens assembly, where it passes through field lens 240 and is collimated by lens 242. The image-bearing light continues through beamsplitter 244 and focus lens 246. It further passes through beamsplitter 248 and plane polarizer 250, and then is focused by camera lens 252 onto the focal plane of video camera 254. Video camera 254 preferably uses a CCD detector although other detectors may be used such as CMOS detectors.

Focus lens 246, shown schematically in FIG. 6 as a single lens element, may alternatively be one or more lens assemblies comprising a plurality of lens elements.

Movement means 266 provides axial movement of focus lens 246 to compensate for different object working distances of the endoscope, allowing it to maintain focus at the video camera focal plane as the endoscope distance from the object is changed. Movement of the lens can be accomplished by manual means, by motors under manual control, or by motors under computer control. Preferably the focus lens 246 utilizes autofocus and an appropriate servomotor to keep the image in proper focus. Such circuitry, furthermore, is well known in the industry so that a further description thereof is unnecessary.

The method here described of sharing the lens tube optical path by both the illumination and the image-bearing light minimizes the required diameter of the endoscope lens tube 202, as there is no requirement for a separate illumination path, and it allows for illumination of an object which is in contact with the stage window 210. Stray light caused by unwanted reflections from lens surfaces may be minimized by the control of the polarization state of the illumination and image-bearing light as next described.

The two polarizers 250 and 264 in the macroscopic path minimize the amount of non-imaging stray light reaching the focal plane of video camera 254. The illumination light is linearly polarized by plane polarizer 264, and the image-bearing light passes through plane polarizer 250. The orientation of polarizer 264 is orthogonal to polarizer 250, ensuring that specular reflections from lens surfaces in the endoscope and housing do not reach the focal plane of the video camera 254. Because light scattered by the object is unpolarized, half of this light is transmitted by polarizer 250 to the camera 254. As an alternative to or in addition to using plane polarizers 250 and 264, beamsplitter 248 may be a polarizing beamsplitter, which transmits light of one polarization and reflects light of the orthogonal polarization.

Microscopic Light Path

A laser preferably located within the housing provides the illumination for the microscopic mode, i.e. imaging on a cellular level. Although other wavelengths can be used, the laser is preferably a laser diode operating at a wavelength of about 950 nm to optimize contrast and tissue penetration.

The microscopic mode includes a confocal optical assembly within its path for high resolution in depth as well as high lateral resolution. In the preferred embodiment, the confocal assembly uses line scanning, but other known methods can be used such as point scanning or Nipkow disk scanning.

With continued reference to FIG. 6, light from a laser diode 290 is focused to a line by cylindrical lens 292. A first slit 294 may be placed at the line focus to clean up the beam as a spatial filter and/or to provide a reference for alignment during manufacture. After passing through slit 294 the illumination passes through plane polarizer 296 and beamsplitter 278. The laser light is then collimated by focus lens 276 and reflected off a first surface of scan mirror 272. After reflection, the illumination light passes through adaptive lens 270, and is reflected by beamsplitter 244. Beamsplitter 244 preferably is provided with a dichroic coating that reflects near-infrared light and transmits visible light. Collimating lens 242 and field lens 240 then direct the illumination light into the lens tube 202, the lenses therein focusing the laser light to a line at the object being examined, this line being an image of the slit 294. In addition, as shown in FIG. 3, the illumination light passes through optical retarder 218 located in the objective lens 212.

To form an image at video camera 288, light reflected by the object is focused by the objective lens 212 and the relay lens or lenses 214 in lens tube 202 to an intermediate image 238. In so doing, the imaging light again passes through the retarder 218 in the objective lens. Image-bearing light from image 238 is redirected by the field lens 240 and collimated by lens 242, reflected by beamsplitter 244, and reflected by the scan mirror 272. An adaptive lens 270 may be provided in the microscope path to correct aberrations caused by index mismatches as described below. The focus lens 276 forms an image of the illuminated line from the object at a second slit 300 after the light has been reflected by beamsplitter 278 and passed through plane polarizer 298. The light passing through the slit 300 is reflected by the mirror 280, collimated by the lens 282, reflected from the mirror 284, and reflected from the second side of scan mirror 272. Camera lens 286 then focuses the line image onto the focal plane of camera 288, which preferably uses a CCD detector although other detectors such as a CMOS detector may be used. The line image becomes a full image as the scan mirror is rotated, synchronously scanning the illumination line across the object and image line across the focal plane of the camera. Any conventional means 274 may be utilized to oscillate the scan mirror about an axis perpendicular to the plane of FIG. 6.

The two polarizers in the housing and the retarder in the objective lens are used to minimize the amount of non-imaging stray light reaching the focal plane of video camera 288. The illuminating laser light is plane polarized after passing through plane polarizer 296. As it passes through the retarder in the objective lens it is changed into circularly polarized light, which then illuminates the object. After returning through the retarder, light specularly reflected by the object will be linearly polarized in a direction perpendicular to the direction of polarization of the illumination light. Light collected from the object then travels back through the imaging system and plane polarizer 298. The polarization direction of polarizer 298 is perpendicular to that of polarizer 296. In this arrangement polarizer 298 eliminates unwanted specular reflections from the lens surfaces up to the retarder, whereas the light reflected by the object is transmitted through the polarizer. In addition or alternatively to polarizers 296 and 298, polarization control may also be implemented by the use of a polarizing beamsplitter 278.

Figure 7A:
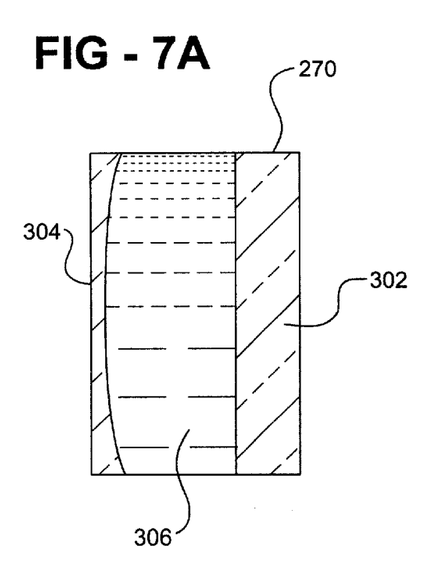
FIGS. 7A and 7B are a diagrammatic view illustrating the adaptive lens of the present invention.
Figure 7B:
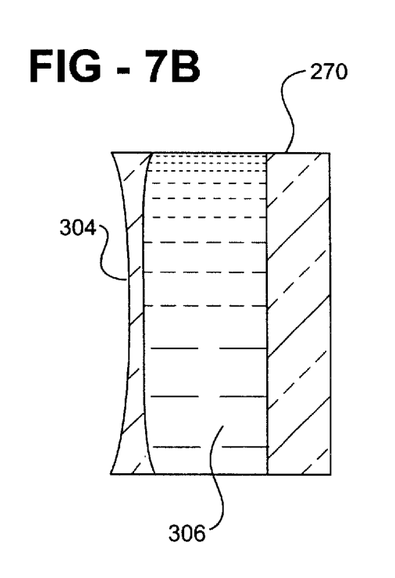

With reference now to FIGS. 7A and 7B, the optional adaptive lens 270 is there shown in greater detail and comprises a rigid window 302, a deformable window 304, and a liquid filled chamber 306 between the windows 302 and 304. By changing the pressure of the liquid 306, the deformable window 304 can be deformed between the positions shown in FIG. 7A and FIG. 7B. The adaptive lens 270 is used to correct optical aberrations introduced as a result of a mismatch of the refractive index of the tissue under examination and of the liquid 222 between the stage window 210 and the lens tube window 215. For a telecentric objective lens 212, the only optical aberration introduced is spherical aberration, which may be corrected by locating the adaptive lens at an image of the aperture stop. The liquid 306 is selected to have the same refractive index as the window material. As the liquid pressure is changed, the deformable window deforms to a predetermined shape to correct spherical aberration. The amount of deformation required can be determined in real time by an algorithm similar to that used for auto focus in the macroscopic mode, with a feedback system adjusting the pressure of the liquid.

In practice, the macroscopic and microscopic light paths are utilized in a mutually exclusive fashion. This may be accomplished by switching power to the alternative light sources, by using shutters to block the optical outputs from the alternative light sources, or by a combination of the two methods.

Figure 8:
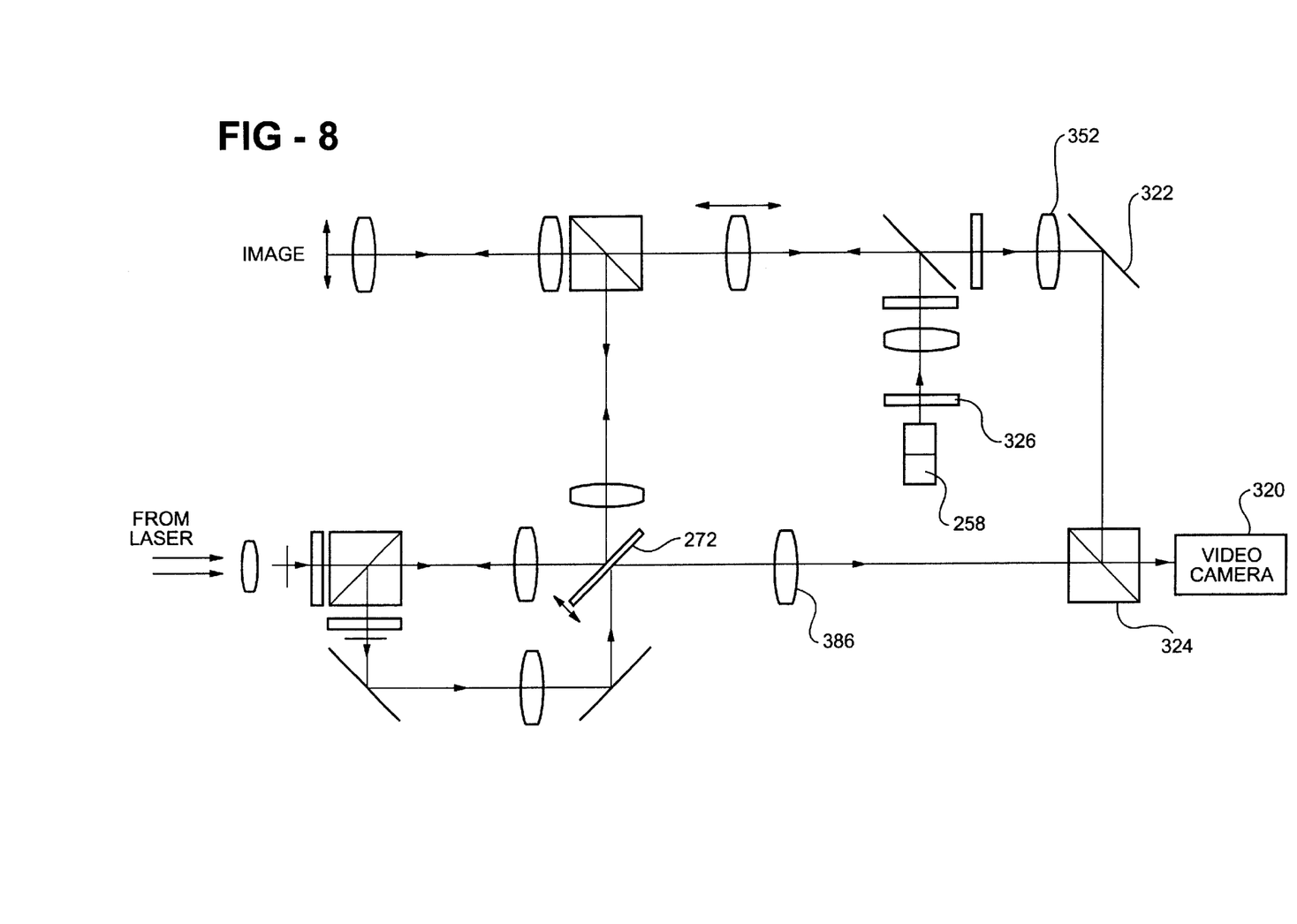
FIG. 8 is an optical diagrammatic view of a second preferred embodiment of the present invention.

With reference now to FIG. 8, an alternative optical configuration for the optics contained within the housing is there shown. The optical configuration shown in FIG. 8 differs from that shown in FIG. 6 in that a single camera 320 is utilized in lieu of the two cameras 288 and 254 shown in FIG. 6. This is accomplished by utilizing a mirror 322 and beam splitter 324 to direct both the white light and the laser image to the camera 320. Other arrangements of mirrors and the beamsplitter are possible to combine the two paths onto a single camera. Preferably a single camera lens is used in the combined path rather than the two separate lenses 352 and 386.

As shown in FIG. 8, an infrared blocking filter 326 is positioned in optical alignment with the input from the macroscopic path light source 258.

Figure 9:
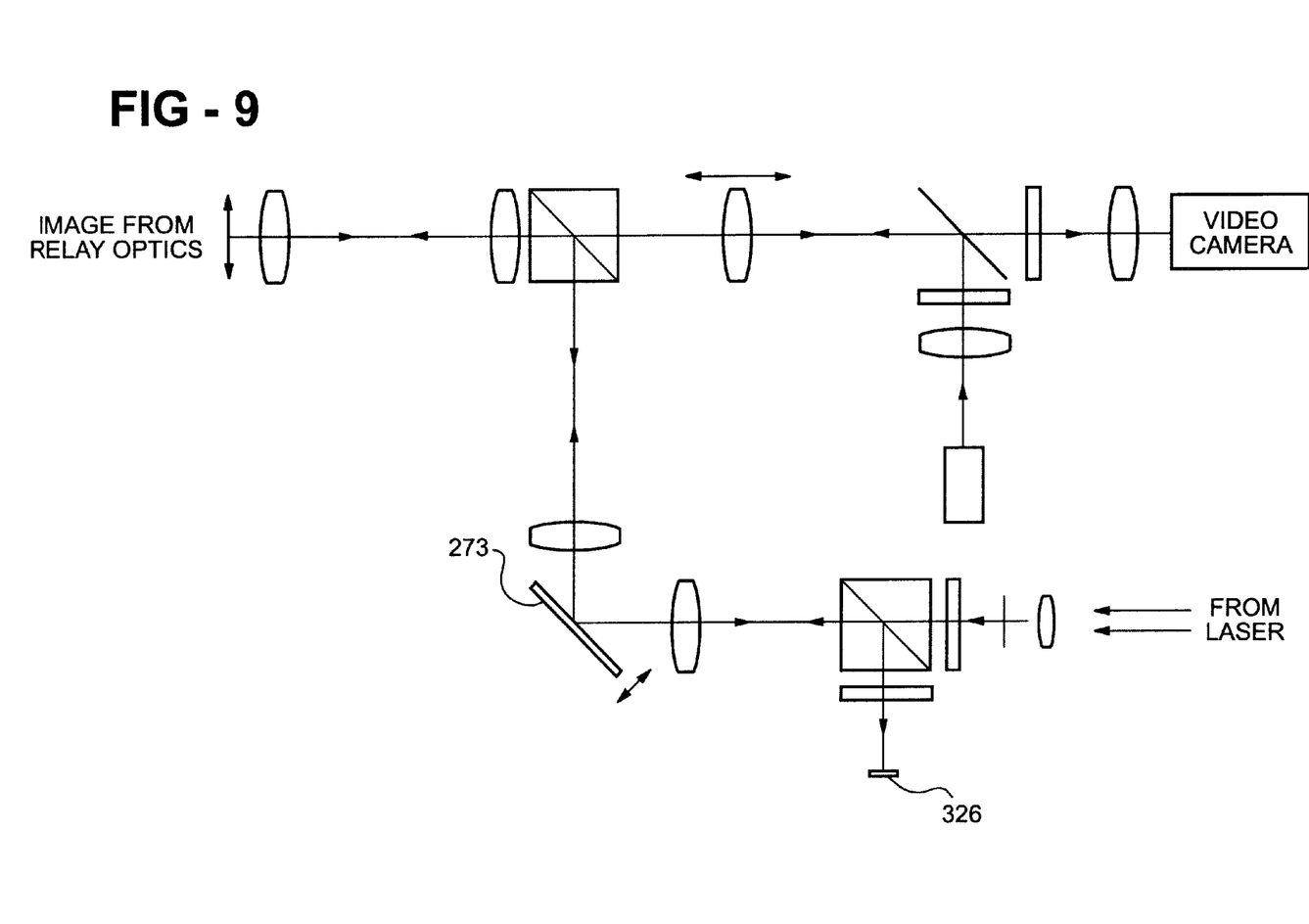
FIG. 9 is an optical diagrammatic view of a housing similar to FIG. 6, but illustrating a modification thereof.

With reference now to FIG. 9, FIG. 9 illustrates yet a further modification of the optical components in the housing 206. The microscopic optical path of FIG. 9 differs from the optical configuration of FIGS. 6 or 8 in that a linear array detector 326 is utilized in lieu of video camera 288. The linear detector 326 is located immediately behind slit 300 of FIG. 6. If the dimensions of the array elements, or pixels, are comparable to the width of the slit, the linear detector can simply be substituted for the slit, as shown schematically in FIG. 9. The long dimension of the detector array is perpendicular to the plane of the drawing in FIG. 9, just as the long dimension of the slit is perpendicular to the plane of the drawing in FIG. 6. The linear detector array receives light from the object along the line of illumination; therefore the linear detector is read out at a rate that corresponds to the scan rate of the illumination line at the object. The detector output signal may be accumulated line-by-line by the external electronic control system, which then develops a formatted two-dimensional electronic image for each complete scan of the object. The image formatting by the electronic control system is performed in synchronism with the object scanning.

The use of the linear detector array eliminates the requirement for the optics, including the scan mirror, associated with the video camera, i.e. the optics between slit 300 and the video camera 288. A scan element 273 having a mirror on one surface only is provided to scan the illuminating line across the object.

It should be understood that the configurations shown in FIGS. 6, 8, and 9 are schematic representations, and that many other configurations may be designed by those skilled in the art to accomplish the same objectives.

Figure 10:
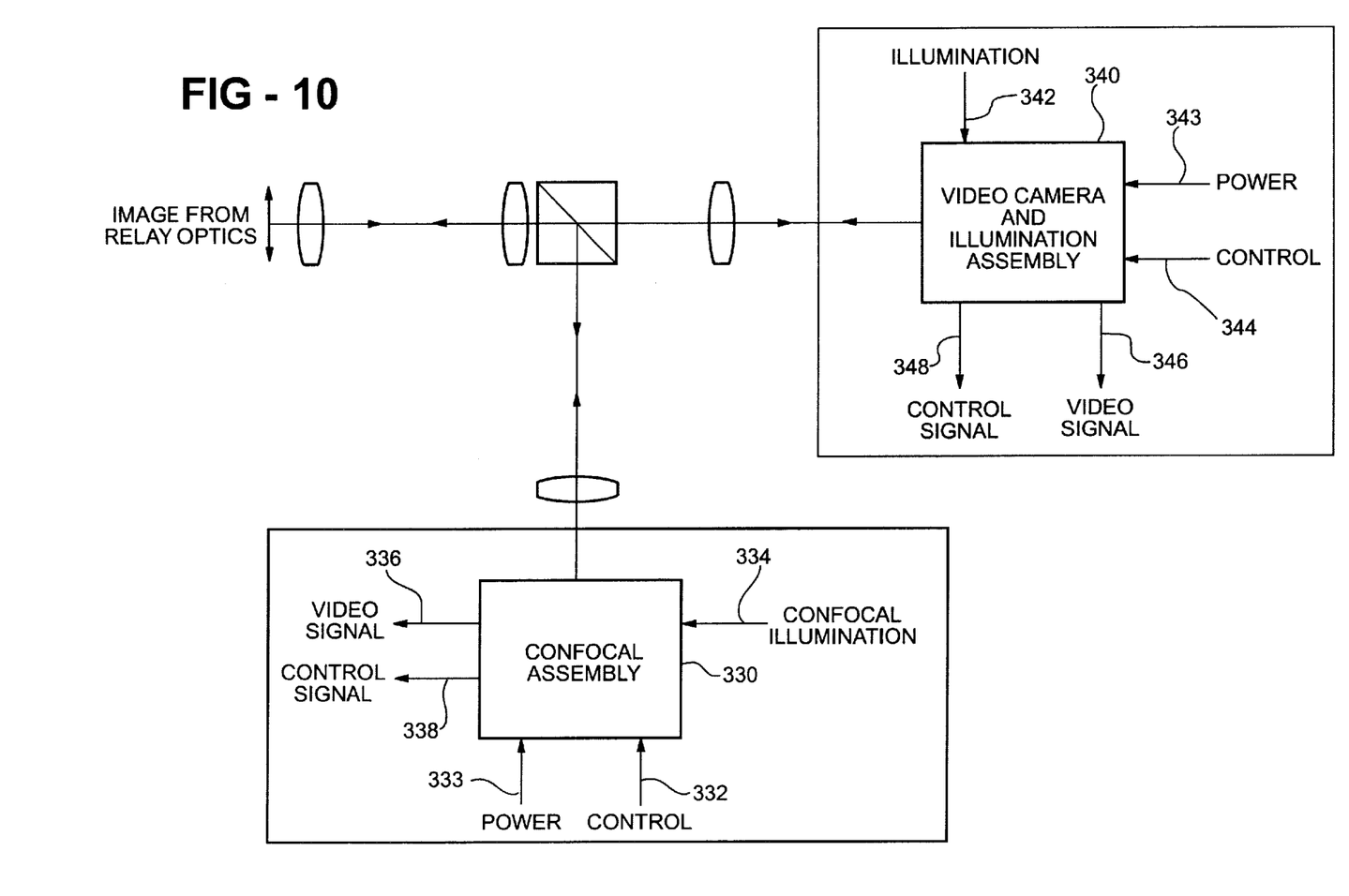
FIG. 10 is a block diagrammatic view showing control circuitry for the preferred embodiment of the invention.

FIG. 10 illustrates in block diagram form the housing lens assemblies with their associated inputs and outputs. In the macroscopic optical path, the video camera and illumination assembly, previously illustrated in detail in FIG. 6, are shown as block 340. White light illumination, preferably provided through an optical fiber cable from an arc lamp external to the housing, is input to block 340 as indicated by line 342. Control signals 344 for operating such elements within block 340 as motors, a shutter, and the video camera are input from one or more computers external to the housing, and electrical power 343 is input from external power supplies. Outputs from block 340 include the video signal 346 from the video camera and control signals 348, which may include feedback signals from positioning motors and a signal that indicates the presence of illumination light.

In the microscopic optical path, the video camera and illumination assembly, previously illustrated in detail in FIG. 6, are shown as block 330. Input illumination 334 is provided by a laser, which may be external to the housing but preferably is located within the housing. As is the case with the macroscopic block 340, inputs to the microscopic block 330 include control signals 332 and electrical power 333. Outputs include the video signal 336 and control signals 338.

Consequently, as can be seen from FIG. 10, both the microscopic imaging mode as well as the white light macroscopic imaging mode can be completely controlled by electronic signals. As a result, remote control of the endoscopic imaging capabilities is possible. For example, a pathologist may control the endoscope over a computer network from a remote location.

In the embodiment described above, the amount of macroscopic magnification is controlled by moving focus lens 246 as the endoscope is moved toward or away from objects within the body cavity.

Figure 11:
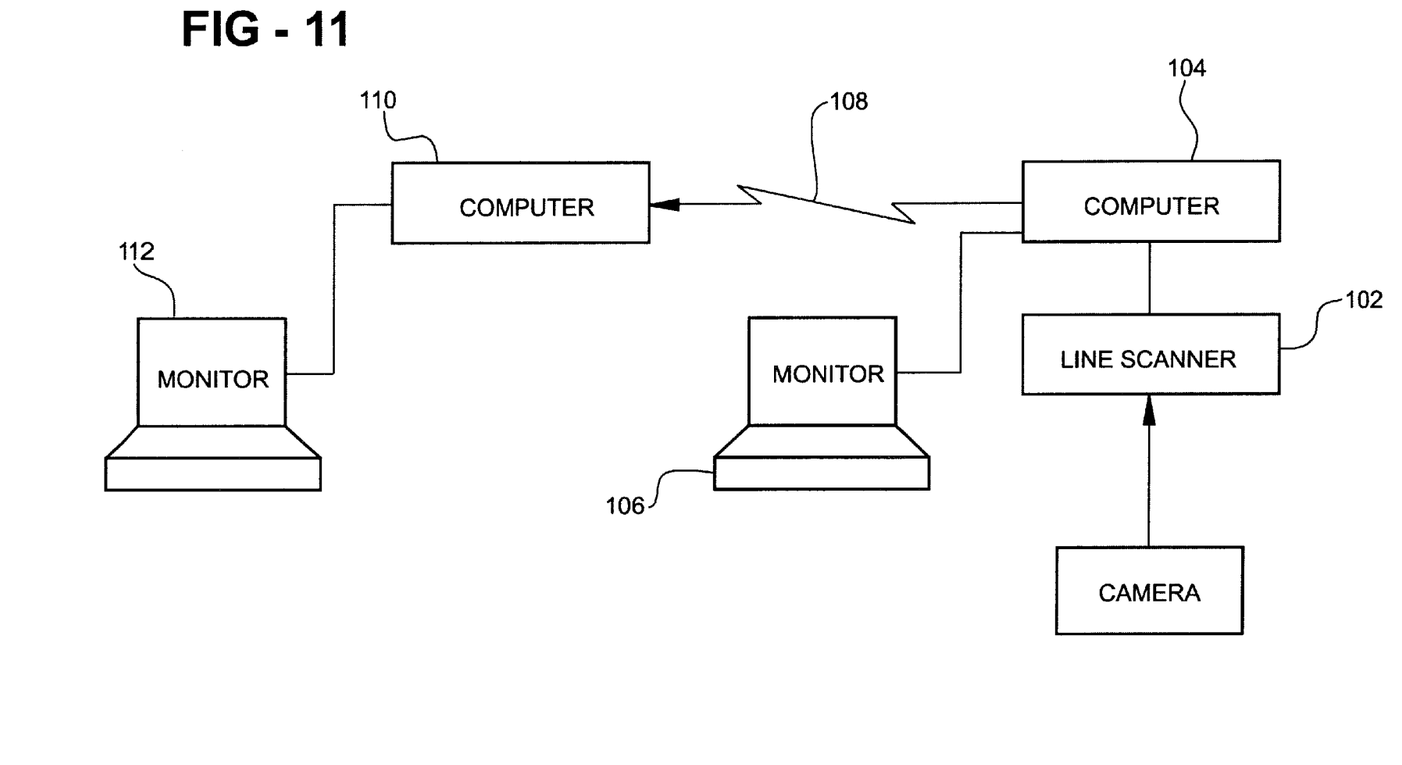
FIG. 11 is a block diagram of the computer and communications system of the present invention.

With reference now to FIG. 11, the video signal from the camera 254, 288 and/or 320, or from the linear detector array 326, is transmitted to a computer system 104. The computer system 104 then displays the image on a monitor 106. The computer system 104, furthermore, is preferably programmed to colorize the image 106 as desired by the medical personnel. The microscopic mode has a much higher intrinsic resolution than the macroscopic mode and may provide an image having more pixels than can be displayed in a single image on the monitor 106. In this case, the computer system may provide an electronic pan and zoom capability to allow the image to be displayed in its full resolution.

In the preferred embodiment of the invention, the computer system 104 electronically communicates via a network 108 to a computer system 110 remote from the endoscope.

The communication network 108 can, for example, comprise telephone lines with modems at each computer system 104 and 110.

In practice, the computer system 104 sends the images to the computer system 110, which then displays these images on its own monitor 112. The monitor 112 can, for example, be viewed by a pathologist to provide a real-time in vivo pathological examination and diagnosis of the target tissue without the necessity of a biopsy or removal of the patient's organ.

As a practical matter, living tissue does not remain stationary during examination. Rather, the tissue moves not only in response to movement of the endoscope, but also in response to cardiac contractions, patient breathing, etc. Consequently, in the preferred embodiment of the invention, the computer system 104 preferably captures and stores a series of sequential images upon command of the medical personnel.

Figure 12:
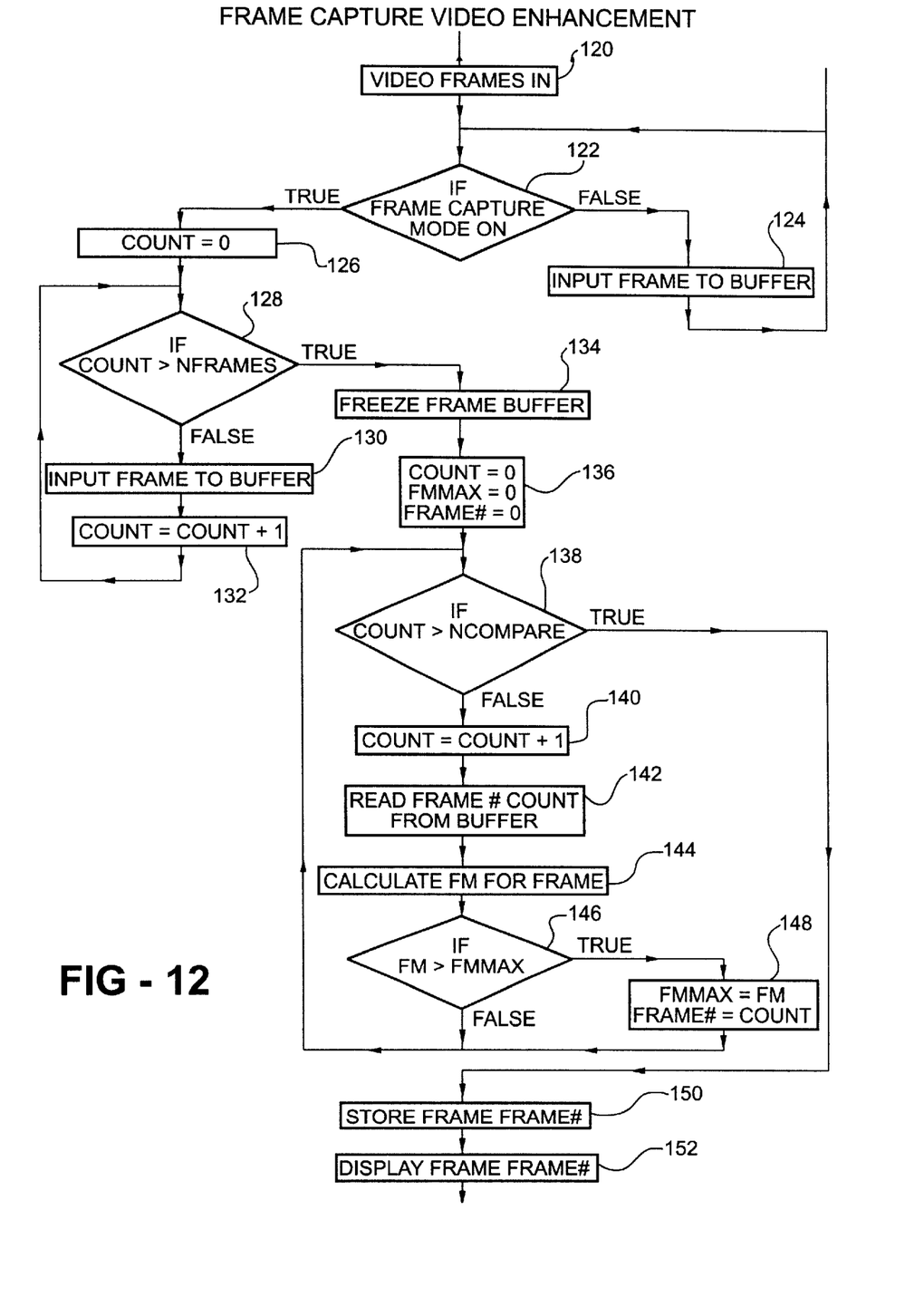
FIG. 12 is a flow chart illustrating the operation of a preferred embodiment of the present invention.

With reference now to FIG. 12, a flow chart for enhancing the video image is there shown. At step 120 a video image is received and step 120 then branches to step 122.

At step 122, the program determines if the frame capture mode is currently activated, i.e. the medical personnel has indicated that an image is desired. If not, step 122 branches to step 124 in which the current input frame is stored to a buffer and step 124 then branches back to step 122.

Conversely, assuming that the video capture mode is activated, step 122 instead branches to step 126 in which the variable COUNT is initialized to zero. Step 126 then branches to step 128.

At step 128, the program determines if the variable COUNT is greater than the variable NFRAMES where NFRAMES equals the number of video frames which are captured following activation of the capture mode. Assuming that COUNT is less than NFRAMES, step 128 branches to step 130 where the frame is input to a memory buffer. Step 130 then branches to step 132 which increments the value of the variable COUNT and step 132 branches back to step 128.

After steps 128–132 have captured the predetermined number of frames, step 128 branches to step 134 which freezes the frame buffer and then to step 136 in which the variables COUNT, FMMAX and FRAME# are all initialized to zero. Step 136 then branches to step 138.

At step 138, the variable COUNT is first compared with the variable NCOMPARE where NCOMPARE equals the number of frames compared from which to choose the capture frame. Initially, COUNT will be less than NCOMPARE so that step 138 branches to step 140 where the variable COUNT is incremented and then to step 142 where the FRAME# corresponding to the variable COUNT is inputted from a buffer. Step 142 then branches to step 144.

At step 144, the program calculates a figure of merit value FM for the frame corresponding to the variable COUNT. Various factors, such as movement of portions of the frame compared to adjacent frame captures, are determined. Step 144 then branches to step 146 where the calculated variable FM is compared to a maximum variable FMMAX. If the currently calculated variable FM exceeds the previously stored variable FMMAX (which will always occur during the first execution of step 146), step 146 branches to step 148 where the variable FMMAX is set to the value of FM and the variable FRAME# is set to the variable COUNT. Step 148 and step 146, in the event that variable FMMAX exceeds the variable FM, both branch back to step 138.

Steps 138–148 iterate until the value of COUNT exceeds the value of NCOMPARE. At that time, the value FM has been calculated for each frame with the frame count of the maximum FM stored in the variable FRAME#. Step 138 then branches to step 150 where the selected video frame FRAME# is stored and then displayed on the monitor at step 152.

In practice the endoscope is placed in macroscopic mode in which it behaves as a standard endoscope that can be used for general observation within a body cavity. In this mode it can be used to locate lesions and other suspect areas for closer examination. Once it has been decided where to look, the surgeon brings the end of the combined stage and lens tube into contact with the target tissue. Using the endoscope imaging path for illumination provides for tissue illumination even with the stage window in contact with the tissue. The endoscope is then switched to microscopic mode, which provides high definition imagery of the tissue surface, and by extending the lens tube into the stage, imagery of thin sections below the surface is provided. The imagery has sufficiently high definition to permit a pathologist to perform an in vivo diagnosis of the target tissue from a computer in a location remote from the operating room.

A further advantage of the present invention is that the detachable stage enables imaging at different layers and depths of the target tissue. Furthermore, since the stage is removable from the lens tube, in practice only sterilization of the stage is required in order to maintain a sterile environment in the patient's body cavity. The stage alternatively may be disposable. In either event complete sterilization of the lens tube and housing is not required.

Having described our invention, however, many modifications thereto will become apparent to those skilled in the art to which it pertains without deviation from the spirit of the invention as defined by the scope of the appended claims.

We claim:

1. An endoscope assembly comprising:
   a housing,
   an elongated lens tube having one end secured to said housing, said lens tube adapted for insertion into a cavity of a body,
   a tube lens assembly contained in said lens tube which optically relays an image from a free end of the lens tube to said housing,
   a housing lens assembly which receives the image from said lens tube,
   camera means which receive the optical image from said housing lens assembly for converting said optical image to an electronic signal,
   means for switching said housing lens assembly between microscopic and macroscopic magnification.

2. The invention as defined in claim 1 and comprising a source of visible light radiation coupled to said housing, a source of infrared radiation coupled to said housing, means for selectively directing radiation from one of said sources from said housing and through said lens tube assembly.

3. The invention as defined in claim 2 wherein said selective directing means comprises a first shutter optically connected in series with said source of visible light and a second shutter optically connected in series with said source of infrared radiation.

4. The invention as defined in claim 1 wherein said housing lens assembly comprises a confocal lens assembly.

5. The invention as defined in claim 4 wherein said confocal lens assembly comprises line scanning imaging means.

6. The invention as defined in claim 1 and comprising means for transmitting said electronic signal exteriorly of said housing.

7. The invention as defined in claim 1 wherein said housing lens assembly comprises means for automatically focusing the image received from said lens tube.

8. The invention as defined in claim 1 wherein said housing lens assembly comprises an adaptive lens.

9. The invention as defined in claim 1 and comprising an elongated tubular stage, said stage being open at one end and having a window disposed across its other end, said open end of said stage slidably disposed over said lens tube, and means for detachably securing said stage to said lens tube adjacent said housing.

10. The invention as defined in claim 9 and comprising means accessible at said housing for longitudinally moving said stage relative to said lens tube between an extended and a retracted position.

11. The invention as defined in claim 10 wherein said window on said stage is longitudinally spaced from the other end of said lens tube thus forming a chamber between said window and said other end of said lens tube, and means for maintaining said chamber filled with a liquid.

12. The invention as defined in claim 11 wherein said maintaining means comprises a bladder disposed in said stage and open to said chamber.

13. The invention as defined in claim 9 wherein said detachable securing means comprises a bayonet coupling.

14. The invention as defined in claim 9 and comprising a collar attached to said stage.

15. The invention as defined in claim 1 and comprising means for recording an image viewed through said lens tube.

16. The invention as defined in claim 15 and comprising means for recording a plurality of sequential images viewed through said lens tube.

17. The invention as defined in claim 16 wherein said recording means comprises a computer having an input, and means for connecting said camera means electronic signal to said computer input.

18. The invention as defined in claim 17 and comprising computer means for storing said images.

19. The invention as defined in claim 17 and comprising means for electronically communicating said images to a location physically remote from the endoscope.

20. The invention as defined in claim 17 wherein said camera means comprises a line scanning imaging means.

21. An endoscope assembly comprising:

a housing, an elongated lens tube having one end secured to said housing, said lens tube adapted for insertion into a cavity of a body, a tube lens assembly contained in said lens tube which optically relays an image from a free end of the lens tube to said housing, a housing lens assembly which receives the image from said lens tube and presents said image exteriorly of said housing, means for switching said housing lens assembly between microscopic and macroscopic magnification in response to an input signal, and means remote from said housing for generating said input signal.

* * * * *